US007010087B2

(12) United States Patent  
Robins

(10) Patent No.: US 7,010,087 B2
(45) Date of Patent: Mar. 7, 2006

(54) DENSITY MEASUREMENT METHOD AND APPARATUS THEREFOR

(75) Inventor: Lee M Robins, Norton (GB)

(73) Assignee: Johnson Matthey PLC, London (GB)

( * ) Notice: Subject to any disclaimer, the term of this patent is extended or adjusted under 35 U.S.C. 154(b) by 177 days.

(21) Appl. No.: 10/291,792

(22) Filed: Nov. 12, 2002

(65) Prior Publication Data
US 2003/0112920 A1    Jun. 19, 2003

Related U.S. Application Data

(63) Continuation of application No. PCT/GB01/01914, filed on May 2, 2001.

(30) Foreign Application Priority Data

May 11, 2000    (GB) .................................... 0011227

(51) Int. Cl.
G01N 23/223 (2006.01)
G01N 23/083 (2006.01)
G01N 23/10 (2006.01)
(52) U.S. Cl. .......................................... 378/57; 378/50
(58) Field of Classification Search ................ 378/57, 378/58
See application file for complete search history.

(56) References Cited

U.S. PATENT DOCUMENTS

| 4,123,654 | A |   | 10/1978 | Reiss et al. |
| 4,393,512 | A | * | 7/1983 | Wang .......................... 378/156 |
| 4,653,081 | A | * | 3/1987 | Sipila et al. ................... 378/45 |
| 4,725,963 | A | * | 2/1988 | Taylor et al. ................. 702/40 |
| 4,980,901 | A | * | 12/1990 | Miller .......................... 378/45 |
| 5,118,940 | A |   | 6/1992 | Davis et al. |
| 5,764,683 | A | * | 6/1998 | Swift et al. .................... 378/57 |
| 6,333,962 | B1 | * | 12/2001 | Kitaguchi et al. ............. 378/57 |
| 6,507,025 | B1 | * | 1/2003 | Verbinski et al. ......... 250/358.1 |

FOREIGN PATENT DOCUMENTS

| GB | 1033789 | 6/1966 |
| GB | 1421755 | 1/1976 |

OTHER PUBLICATIONS

Friggens et al. "Nuclear Gages Applied to a Pressurized Gas Producer for Location of Coal Bed Level and Combustion Zone" *Advances in Instrumentation, Proceedings of the 25th Annual ISA Conference* (Oct. 1970) pp. 8041-8043 -- Accession No. XP-002195038.

* cited by examiner

*Primary Examiner*—Craig E. Church
*Assistant Examiner*—Krystyna Suchecki
(74) *Attorney, Agent, or Firm*—Mayer Brown Rowe & Maw LLP

(57) ABSTRACT

The density of a mass of material is determined by passing radiation from a source, such as Co-60, whose radiation spectrum has a characteristic energy level above 700 keV through the mass of material to a detector that can detect radiation at a energy level, or range of energy levels, within the range 80 to 700 keV. By determining the density of the mass of material at different locations, the density profile of the mass of material can be assessed.

18 Claims, 2 Drawing Sheets

DENSITY MEASUREMENT METHOD AND APPARATUS THEREFOR

CROSS REFERENCE TO RELATED APPLICATION

This application is a continuation of International Application No. PCT/GB01/01914, filed May 2, 2001. This application, in its entirety, is incorporated herein by reference.

The present invention relates to a method of measuring the density of a material in bulk form and in particular to a method of detecting chances in the density of a material in the bulk.

Measurement of density of a material within an enclosed vessel or pipe may be used to detect the location and nature of interfaces between materials of different densities. Such measurement may be carried out by means of passing penetrating radiation from a source through the material and measuring the intensity of the radiation which impinges upon a radiation detector which is located at a distance from the source of the radiation. The radiation used is often gamma radiation. This method of density measurement has found a wide variety of applications, particularly in materials processing industries such as chemicals or food manufacturing. Examples of applications of this general technique are level detection in vessels containing materials of different densities, e.g. liquids and vapours, measurement of the density profile of distillation columns to detect columns trays, liquid and vapour levels etc.

A problem found with conventional radiation scanning techniques occurs when large masses of dense material need to be measured, for example when the density changes within a large vessel packed with a solid material are to be measured. In these circumstances, much of the radiation may be absorbed by the material so that relatively little is detected by the radiation detector, making density measurement, and in particular measurement of changes in density, very difficult or impossible. Although in theory this difficulty might be overcome by the use of a stronger source of radiation, in practice, because the absorption of radiation is exponentially related to the strength of the source, the source selected would need to be too powerful to be used safely without significant disruption to the surrounding areas.

Other options, such as introducing the radiation source or detector into the mass of material to be measured may be used to reduce the path-length between the source and detector, but such techniques may require a more permanent installation and may be inconvenient for installation within some types of vessels, e.g. reactors having fixed beds of catalysts or absorbents.

It is therefore desirable to use a method and apparatus for measuring the density of large masses of dense material which is non invasive and which may be used safely in process plant areas with only minimal disruption.

Radiation sources such as cobalt-60 emit radiation over an energy spectrum having one or more characteristic energy levels. Conventional density measurement systems involve determining the attenuation, caused by the material under examination, of the radiation at one or more of those characteristic energy levels. Where the radiation has to pass a substantial distance through the material under examination, the attenuation of the radiation having those characteristic energy levels may be substantially complete. However we have found that radiation at lower energy levels than those characteristic levels can be detected and used to determine densities. Although we do not wish to be bound by the following explanation, it is thought that the detected lower energy level radiation may result from absorption of energy at the higher energy levels by the material under examination and emission at a lower energy level and/or by multiple reflections from the material under examination. Whereas examination of the energy spectrum of radiation from a source in the absence of significant absorption reveals peaks corresponding to the aforesaid characteristic levels, and broad, diffuse, amounts of radiation at other energy levels, we have found that after passage through a test material that effects significant attenuation of the radiation at energy levels above 700 keV, one or more peaks may be detected at lower energy. The energy level corresponding to these lower energy level peaks may differ depending upon the nature of the test material. Thus examination of the radiation at the lower energy levels can be used to determine the density.

According to the invention we provide a method of measuring the change in density of a material comprising the steps of:
a) positioning a source of penetrating radiation having one or more characteristic energy levels above 700 keV such that the radiation is directed through a portion of the material;
b) positioning a radiation detector in alignment with said source, thereby to detect the radiation which has passed through said portion of the material;
c) passing the signal from said radiation detector to a spectrum analyser which is capable of providing a measurement of the radiation intensity over at least part of the energy spectrum from 80 keV to 700 keV, and
d) detecting changes in the intensity and/or energy of detected radiation at at least one energy level within the range 80 keV to 700 keV.

According to a second aspect of the invention, we also provide a method of determining the density profile of material within a vessel comprising positioning a source of penetrating radiation having one or more characteristic energy levels above 700 keV adjacent said vessel at a first location, positioning a radiation detector adjacent said vessel in alignment with said source to detect radiation at at least one energy level in the range 80 keV to 700 keV that has passed through a portion of said material at said first location, determining the intensity and/or energy level of said radiation at said energy level within said range, moving said source and detector to a second location from said first location and determining the intensity and/or energy level of said radiation at said at least one energy level in said range at said second location, and comparing the determined intensities and/or energy levels and thereby determining the density of said material at said second location relative to its density at the first location.

According to a third aspect of the invention we provide apparatus for measuring the density of a material comprising a source of penetrating radiation having one or more characteristic energy levels above 700 keV, adapted to enable a beam of radiation to be directed into and through said material; a radiation detector which is capable of detecting radiation in at least one range of energy levels within the range 80 to 700 keV and a spectrum analyser which is arranged to receive a signal from said radiation detector and which is capable of providing measurements of radiation intensity over said at least one range.

The radiation source is preferably a source of gamma-radiation. Suitable sources include sodium-24 or, more preferably, cobalt-60. The strength of the source used is preferably in the range 1–15 GBq, more preferably 3–10 GBq.

The radiation detector is a standard unit, known in the art, which typically comprises a crystal, normally of sodium iodide, having a dimension of about 25–100 mm, more usually approximately 50–75 mm, coupled to a scintillation detector or photo multiplier tube.

As indicated above, in a typical gamma-scanning device of the prior art, the radiation detector is connected to a simple rate-meter to measure the intensity of radiation received in the high energy part of the energy spectrum. For example, the main energy peaks for the most common isotope used, cobalt-60, are at the 1173 keV and 1332 keV positions on the gamma spectrum. In the apparatus and method of the present invention the output from the radiation detector is preferably fed to a spectrum analyser. The latter is preferably capable of providing radiation intensity information over the full spectrum between about 80 and 1600 keV but is at least capable of providing radiation intensity information over a range of energy levels within the range between about 80 and about 700 keV. As indicated above, although the high-energy radiation, which is normally monitored for conventional density difference measurement, may be attenuated to such an extent on passage through large volumes of dense material that it cannot be detected satisfactorily, it is possible to detect changes in lower energy levels of the radiation spectrum which vary according to the density of material through which the radiation has passed.

The detector should be capable of detecting radiation at at least one energy level within the range 80 to 700 keV. Unless it is known from previous experience that the particular material under investigation will give a meaningful measurement at a particular energy level, in which case the detector need only monitor that energy level, it is preferred that the detector is responsive to radiation over a range of energy levels, preferably at least the range 100 to 300 keV. In a preferred form of the invention the radiation detector is used in combination with a spectrum analyser so that the variation of the detected radiation intensity with the radiation energy level can be determined and compared with a similar spectrum obtained with the source and detector at another location along the length of the vessel. Preferably the spectrum analyser integrates the detected radiation over a range of energy levels and comparison of the integral obtained at one location is compared with the integral obtained at another location to give an indication of the change in density of the vessel contents.

The radiation passing through the material at any one position is normally monitored for a fixed period of time to ensure that sufficient radiation is collected for a representative result to be collected and passed to the spectrum analyser. The time of collection may be varied according to the path length between the source and the detector, relative strength of the radiation source, density of the material etc. We have found that a monitoring period of about 30–200 seconds, e.g. 60–120 seconds. at each location is usually sufficient. The method of the invention has been found to be particularly useful for remnant bed life measurement, i.e. to detect density changes in a bed of catalyst or absorbent material which reflect the amount of useful life left in the bed. An example of this application is found in the use of zinc-containing sulphur absorbents for the removal of hydrogen sulphide from natural gas streams as a precursor to the treatment of the gas in e.g. a steam reformer. The sulphur absorbent comprises a zinc compound, such as zinc oxide, which reacts with the hydrogen sulphide to produce zinc sulphide and water. In practice the sulphur removal arrangement often comprises hydrodesulphurisation in combination with hydrogen sulphide absorption. Thus the feedstock, to which some hydrogen has been added, may be passed, at an elevated temperature, through a first bed of a pelleted zinc oxide absorbent to absorb any hydrogen sulphide in the feedstock. The treated feedstock is then passed through a bed of a pelleted hydrodesulphurisation catalyst, e g. a nickel and/or cobalt molybdate wherein any organic sulphur compounds present are hydrogenated: the sulphur in the organic compounds is converted to hydrogen sulphide. The hydrodesulphurised feedstock is then passed through a further bed of a pelleted zinc oxide absorbent to absorb the hydrogen sulphide formed in the hydrodesulphurisation step. The zinc oxide gradually changes to zinc sulphide and it is possible to detect the transition between the oxide and sulphide by the difference between the density of zinc oxide (approx. 1200 $kg/m^3$) and that of zinc sulphide (approx. 1400 $kg/m^3$). Replacing a bed with fresh zinc oxide is an expensive operation and may be costly and wasteful if done before the bed is fully exhausted. It is therefore desirable to monitor the amount of zinc oxide in the bed and this is conveniently achieved by the method and using the apparatus of the invention. In a typical plant, the vessels may be relatively large, for example about 2 m in diameter and, since the process is generally operated at an elevated pressure, e.g. 30 bar abs., the vessels will have relatively thick walls, typically having a wall thickness of about 50 mm or more. Conventional gamma-scanning techniques are not capable of penetrating through the vessel.

Clearly the method and apparatus may be applied to a variety of end-uses in which density monitoring can be applied.

The method of the invention is not invasive. The radiation source and detector must be aligned so that radiation can pass from the source, through at least a portion of the material, to the detector and therefore in use, the detector is located opposite the source with the material to be measured between the two. In a typical application, the material to be measured is contained within a vessel such as a tank or a reactor vessel. The radiation source is placed adjacent an external surface of the vessel so that the radiation shines into the vessel. The detector is placed adjacent a different part of the external surface directly opposite the radiation source so that it collects and detects radiation which has travelled from the source through the vessel and any material contained therein. The optimum placement of the detector and source can be determined by experiment. We have found that when the vessel is cylindrical, for example, in some cases it may be preferable to arrange the source and detector along the line of a chord across a portion of the transverse cross-section, rather than to place them at opposed ends of a diametrical path. When the measurements have been made at one location, e.g. one chord or diameter, the source and detector are then moved to another location, e.g. displaced in a direction of the longitudinal axis of the vessel, and measurements taken at that second location. By comparison of the detected radiation at the first and second locations, the density of the material under test at one location can be compared to that at the other location. In some cases it may be desirable to make measurements at different chords or diameters at the same position along the longitudinal axis of the vessel.

By moving the source and detector along or around a vessel, changes in the mean bulk density of the material contained within different parts of the vessel can be determined. In a cylindrical or other elongated vessel, it is useful to measure the density at incremental distances along the vessel by moving the source and detector along the vessel by the same amount after each measurement, in order to generate a density profile of the material contained within. In the example already described of a zinc oxide bed, the zinc oxide is normally used up from one end of the vessel following the path of the gas passing through and the transition between ZnO and ZnS therefore moves along the vessel over time. By taking measurements of material density along the length of the vessel, the position of the transition between the two materials can be located and the amount of zinc oxide remaining and thus the remaining life of the bed can be estimated.

The detector and source may be permanently fixed to a vessel containing the material to be measured or they may be temporarily secured or held adjacent to the vessel. The detector and source may be mounted moveably, e.g. on tracks or a suspension system so that they may be moved along or around the surface of the vessel. Alternatively they may be fixed to a mechanical handling device and moved manually between measurements. More than one pair of source and detector may be provided to measure the density through different parts of the vessel simultaneously or sequentially.

The spectrum analyser may be mounted within housing containing the detector or may be located remotely from the detector. The spectrum analyser may receive a signal from one or more than one detector. The signal is carried between the detector and the spectrum analyser by any suitable means, e.g. by means of a cable, wire or by a wire-less transmission method, e.g. radio-waves.

The apparatus may be adapted to be readily portable so that it may be assembled and aligned with the vessel to collect data at the location of the vessel to be measured and then transported to a different location. In this form the apparatus preferably includes a power supply for the detector and spectrum analyser.

Alternatively, the apparatus may be fixed or semi-fixed in position, i.e. securely mounted about a vessel in such a way as to be moveable to measure the density at different locations within the vessel. In this form the output from the spectrum analyser may be fed to a reactor control system or displayed in a control room.

The output from the spectrum analyser may be displayed or printed for analysis and interpretation by an operator or it may be fed to a computer program for interpretation and output directly as a density measurement.

An example of the invention will now be further described, with reference to the accompanying drawings in which FIGS. 1A and 1B are schematic vertical and horizontal cross sections respectively of the apparatus of the invention in use during a remnant life analysis application;

Figure 1A:
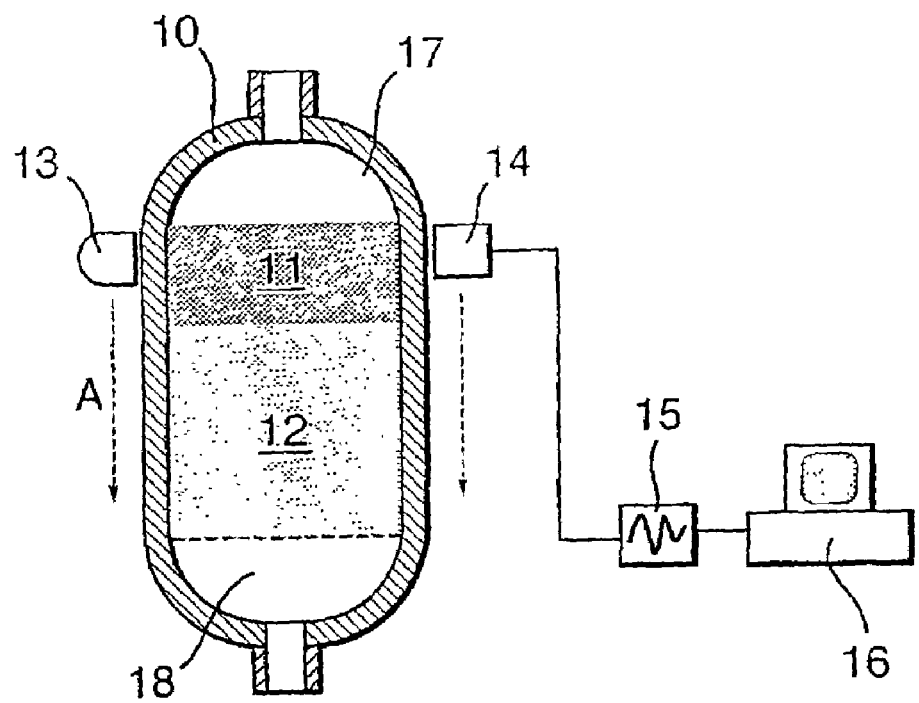
Figure 1B:
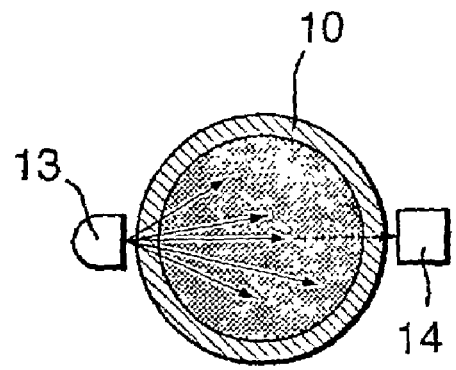

Using an arrangement as shown in FIGS. 1A and 1B, the change in density of a zinc oxide (11, 12) bed of 7.0 m height, within a 2.6 m diameter steel vessel (10), having a wall thickness of 60 mm installed in the feedstock purifation stage of an ammonia plant was investigated. The vessel had a coating of approximately 60 mm of lagging.

A 80 milliCurie (mCi) (3 GBq) Co-60 radioactive source (13) and a scintillation detector (14), comprising a 2 inch (50 mm) sodium iodide crystal and photomultiplier tube, were placed on opposite sides of the vessel, at the same known elevation above the catalyst bed. The scintillation detector was connected by 30 metres of co-axial cable to a spectrum analyser (15) (Model: 92X Spectrum Master, Manufacturer: EG&G Ortec), connected to a personal computer (16) running 'Maestro' analysis software supplied by EG&G Ortec.

The radiation intensity in the full gamma spectrum was then recorded for 100 seconds and saved as a data file within the analysis software. The source and detector were then lowered in 100 mm increments down the bed in the direction of the arrow A, and the gamma spectrum recorded at each position to a point below the bed.

After all of the data was collected, the gamma spectrum at each elevation was analysed to determine the presence of any repeatable incremental changes through the length of the bed. Observed changes were seen over a small area between the 80 keV and 700 keV energy level region. A typical spectrum is shown in FIG. 2 where it is seen that while significant radiation could be detected over energy levels ranging from about 100 to 250 keV, the radiation detected at the Co-60 characteristic energy levels, viz. 1173 and 1332 keV, was negligible.

Figure 2:
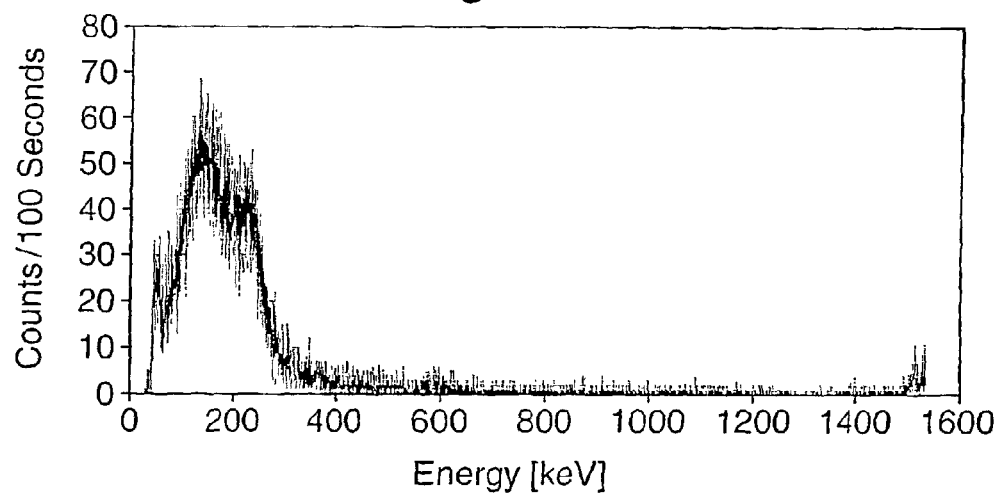
FIG. 2 is a typical spectrum of the detected radiation.
Figure 3:
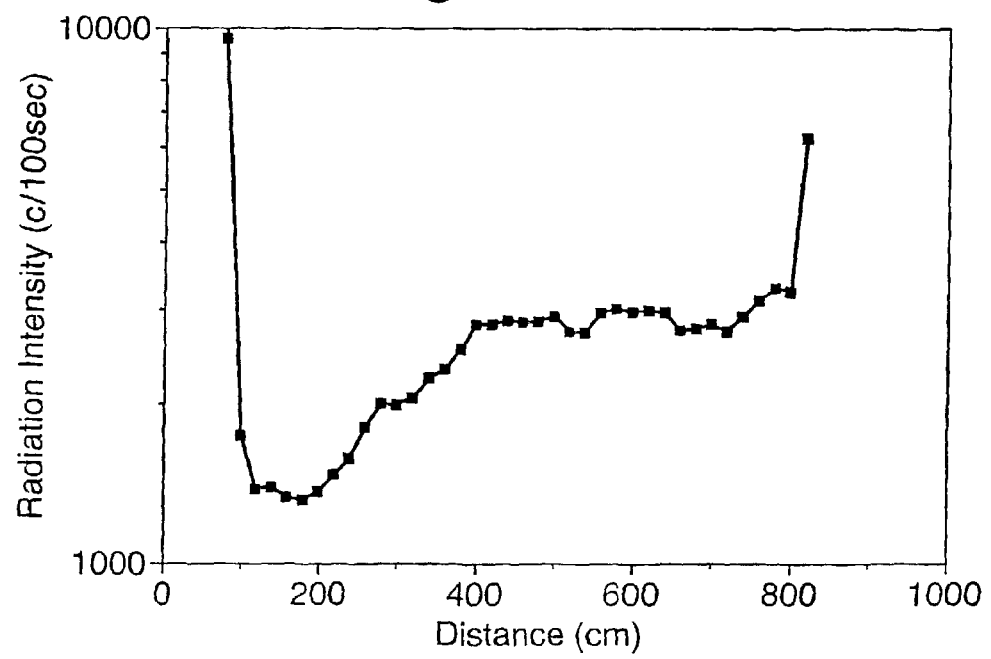
FIG. 3 is a graphical representation of the density change at increments along the absorbent bed.

The radiation intensity in the energy level range 100 to 300 keV was integrated, and a graphical representation against distance down the vessel produced, as shown in FIG. 2.

The graph shows that the greatest mean density of material was observed at the top of the bed, and this density was constant for approximately 1 m down the bed. This density then gradually reduced for a further 2 m of the bed, after which there was an approximately constant density region for the remaining 4 m of the bed. This can be interpreted as sulphided absorbent (11) at the top of the bed for 1 m, which gradually reduces in density over approximately 2 m, at which point the start of the remaining clean zinc oxide (12) was observed. The remaining 4 m of the bed appears to consist of clean zinc oxide. The mean density is seen to significantly decrease above and below the bed due to the vapour regions (17, 18).

What is claimed is:

1. A method of determining the density profile of material within a vessel comprising positioning a source of penetrating radiation having its characteristic energy level, or levels at above 700 keV adjacent said vessel at a first location, positioning a radiation detector adjacent said vessel in alignment with said source to detect radiation at at least one energy level in the range 80 keV to 700 keV that has passed through a portion of said material at said first location, determining the intensity and/or energy level of said radiation at said energy level within the range from 80 keV to 700 keV, moving said source and detector to a second location displaced from said first location and determining the intensity and/or energy level of said radiation at said at least one energy level in the range from 80 keV to 700 keV at said second location, and comparing the determined intensities and/or energy levels in the range from 80 keV to 700 keV and thereby determining the density of said material at said second location relative to its density at the first location.

2. A method according to claim 1 wherein the radiation source is cobalt-60.

3. A method according to claim 2 wherein said source has a strength in the range 1–15 GBq.

4. A method according to claim 1 wherein the source and detector are disposed at the ends of a chord, or diameter, through the vessel in a plane perpendicular to the longitudinal axis of the vessel.

5. A method according to claim 4 wherein, after determining the intensity and/or energy level of the radiation at a first chordal or diametrical location, the source and detector are moved to a second location displaced from first location in the direction of the longitudinal axis of the vessel.

6. A method according to claim 1 wherein the material is a zinc-containing sulphur-absorbent material.

7. A method of measuring the change in density of a material comprising the steps of:
  a) positioning a source of penetrating radiation having its characteristic energy level, or levels, at above 700 keV such that the radiation is directed through a portion of the material;
  b) positioning a radiation detector in alignment with said source, thereby to detect the radiation which has passed through said portion of the material;
  c) passing the signal from said radiation detector to a spectrum analyser which is capable of providing a measurement of the radiation intensity over at least part of the energy spectrum from 80 keV to 700 keV, and
  d) detecting changes in the intensity and/or energy of detected radiation at at least one relatively low energy portion of the spectrum in the range 80 keV and 700 KeV.

8. A method according to claim 7, wherein, when the intensity of detected radiation has been determined at a first location, the source and detector are moved to a different location and the intensity of detected radiation is determined at the new location.

9. A method according to claim 8, wherein the material is contained within a vessel having a longitudinal axis and said first and second locations are displaced from one another along the longitudinal axis of the vessel.

10. A method according to claim 8, wherein the material is contained within a vessel having a longitudinal axis and said first and second locations are at different chords or diameters at the same position along the longitudinal axis of the vessel.

11. An apparatus for measuring the density of a material comprising a source of penetrating radiation having its characteristic energy level or levels at above 700 keV, for enabling a beam of radiation to be directed into and through said material; a radiation detector for of detecting radiation in at least one range of energy levels within the range 80 to 700 keV and a spectrum analyser for receiving a signal from said radiation detector and for providing measurements of radiation intensity over said at least part of one range for determining the density of said material from the intensity of radiation having an energy in the range from 80 keV to 700 keV which is measured by said radiation detector.

12. An apparatus according to claim 11 wherein the radiation source is cobalt-60.

13. An apparatus according to claim 11 wherein the radiation source has a strength in the range 1–15 GBq.

14. An apparatus according to claim 11, wherein the source and detector are mounted moveably such that they may be moved along or around the surface of a vessel within which said material is contained.

15. An apparatus according to claim 11, wherein the source and detector are permanently fixed to a vessel containing the material to be measured.

16. An apparatus according to claim 11 comprising more than one pair of source and detector.

17. An apparatus according to claim 11 which is adapted to be readily portable between locations.

18. An apparatus according to claim 11 further comprising a power supply.

* * * * *